US011109853B2

(12) United States Patent
Zajac et al.

(10) Patent No.: US 11,109,853 B2
(45) Date of Patent: Sep. 7, 2021

(54) ADJUSTABLE SELF-LOCKING LOOP CONSTRUCTS FOR TISSUE REPAIRS AND RECONSTRUCTIONS

(71) Applicant: ARTHREX, INC., Naples, FL (US)

(72) Inventors: Eric S. Zajac, Naples, FL (US); Jacob A. Jolly, Naples, FL (US)

(73) Assignee: ARTHREX, INC., Naples, FL (US)

( * ) Notice: Subject to any disclaimer, the term of this patent is extended or adjusted under 35 U.S.C. 154(b) by 256 days.

(21) Appl. No.: 16/371,381

(22) Filed: Apr. 1, 2019

(65) Prior Publication Data

US 2019/0223858 A1 Jul. 25, 2019

Related U.S. Application Data

(62) Division of application No. 13/647,549, filed on Oct. 9, 2012, now Pat. No. 10,245,016.

(Continued)

(51) Int. Cl.
*A61B 17/04* (2006.01)
*A61F 2/08* (2006.01)
(Continued)

(52) U.S. Cl.
CPC ...... *A61B 17/0401* (2013.01); *A61B 17/0469* (2013.01); *A61F 2/0811* (2013.01); *A61B 17/0487* (2013.01); *A61B 17/06* (2013.01); *A61B 2017/0404* (2013.01); *A61B 2017/0417* (2013.01); *A61B 2017/06185* (2013.01); *A61F 2/0095* (2013.01); *A61F 2002/087* (2013.01); *A61F 2002/0852* (2013.01); *A61F 2002/0882* (2013.01)

(58) Field of Classification Search
CPC ........ A61B 17/0401; A61B 2017/0404; A61B 2017/06185; A61B 17/0469; A61B 17/06; A61F 2/0811; A61F 2002/0852; A61F 2002/087; A61F 2002/0882
See application file for complete search history.

(56) References Cited

U.S. PATENT DOCUMENTS 3,176,316 A 4/1965 Bodell
4,187,558 A 2/1980 Dahlen et al.
(Continued)

FOREIGN PATENT DOCUMENTS

DE 29910202 U1 9/1999
DE 20101791 U1 6/2001
(Continued)

OTHER PUBLICATIONS

Extended European Search Report for Application No. EP 12 18 8229 dated Feb. 6, 2013.

*Primary Examiner* — Alexander J Orkin
(74) *Attorney, Agent, or Firm* — Carlson, Gaskey & Olds

(57) ABSTRACT

Systems and methods for bone to bone, or soft tissue to bone, repairs without knot tying. The repair systems include self-cinching constructs which are tensionable and which include a flexible strand with a knotless, adjustable loop with at least one splice and a shuttle/pull device attached to the flexible strand. A final splice is formed by pulling on the shuttle/pull device subsequent to the knotless, adjustable loop being assembled with or secured to tissue (for example, a soft tissue graft or BTB graft), to allow desired tensioning of the graft to be fixated relative to the bone.

15 Claims, 18 Drawing Sheets

Related U.S. Application Data

(60) Provisional application No. 61/546,305, filed on Oct. 12, 2011.

(51) Int. Cl.
*A61F 2/00* (2006.01)
*A61B 17/06* (2006.01)

(56) References Cited

U.S. PATENT DOCUMENTS

| | | |
|---|---|---|
| 4,301,551 A | 11/1981 | Dore et al. |
| 4,400,833 A | 8/1983 | Kurland |
| 4,776,851 A | 10/1988 | Bruchman et al. |
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,026,398 A | 6/1991 | May et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,540,703 A | 7/1996 | Barker, Jr. et al. |
| 5,562,669 A | 10/1996 | McGuire |
| 5,575,819 A | 11/1996 | Amis |
| 5,628,756 A | 5/1997 | Barker, Jr. et al. |
| 5,643,266 A | 7/1997 | Li |
| 5,645,588 A | 7/1997 | Graf et al. |
| 5,931,869 A | 8/1999 | Boucher et al. |
| 5,961,520 A | 10/1999 | Beck, Jr. et al. |
| 5,964,764 A | 10/1999 | West, Jr. et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 | 2/2001 | Seedhom |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom, Jr. et al. |
| 6,517,578 B2 | 2/2003 | Hein |
| 6,533,802 B2 | 3/2003 | Bojarski et al. |
| 7,097,654 B1 | 8/2006 | Freedland |
| 7,306,417 B2 | 12/2007 | Dorstewitz |
| 7,494,506 B2 | 2/2009 | Brulez et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,057 B2 | 1/2011 | Cook et al. |
| 7,905,903 B2 | 3/2011 | Stone et al. |
| 7,914,539 B2 | 3/2011 | Stone et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 2001/0041938 A1 | 11/2001 | Hein |
| 2002/0161439 A1 | 10/2002 | Strobel et al. |
| 2002/0165611 A1 | 11/2002 | Enzerink et al. |
| 2002/0173788 A1 | 11/2002 | Bojarski et al. |
| 2003/0023268 A1 | 1/2003 | Lizardi |
| 2003/0114929 A1 | 6/2003 | Knudsen et al. |
| 2004/0002734 A1 | 1/2004 | Fallin et al. |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137624 A1 | 6/2005 | Fallman |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0067971 A1 | 3/2006 | Story et al. |
| 2006/0079904 A1 | 4/2006 | Thal |
| 2006/0095130 A1 | 5/2006 | Caborn et al. |
| 2006/0142769 A1 | 6/2006 | Collette |
| 2006/0190041 A1 | 8/2006 | Fallin et al. |
| 2006/0259076 A1 | 11/2006 | Burkhart et al. |
| 2006/0265064 A1 | 11/2006 | Re et al. |
| 2007/0021839 A1 | 1/2007 | Lowe |
| 2007/0049944 A1* | 3/2007 | Stone ............... A61B 17/0401 606/86 A |
| 2007/0083236 A1 | 4/2007 | Sikora et al. |
| 2007/0118217 A1 | 5/2007 | Brulez et al. |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0185532 A1 | 8/2007 | Stone et al. |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0046009 A1 | 2/2008 | Albertorio et al. |
| 2008/0177302 A1 | 7/2008 | Shurnas |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0255613 A1 | 10/2008 | Kaiser et al. |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1 | 12/2008 | Denham et al. |
| 2009/0018654 A1 | 1/2009 | Schmieding et al. |
| 2009/0030516 A1 | 1/2009 | Imbert |
| 2009/0054928 A1* | 2/2009 | Denham ............ A61B 17/0401 606/232 |
| 2009/0054962 A1 | 2/2009 | Lefler et al. |
| 2009/0062854 A1 | 3/2009 | Kaiser et al. |
| 2009/0082805 A1 | 3/2009 | Kaiser et al. |
| 2009/0187244 A1 | 7/2009 | Dross |
| 2009/0216326 A1 | 8/2009 | Hirpara et al. |
| 2009/0228017 A1 | 9/2009 | Colllins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2009/0318961 A1 | 12/2009 | Stone et al. |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145114 A1 | 6/2010 | Abhari et al. |
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0274355 A1 | 10/2010 | McGuire et al. |

(56) References Cited

U.S. PATENT DOCUMENTS

| | | | |
|---|---|---|---|
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0041938 A1 | 2/2011 | Parks |
| 2011/0046734 A1 | 2/2011 | Tobis et al. |
| 2011/0054609 A1 | 3/2011 | Cook et al. |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165938 A1 | 6/2012 | Denham et al. |
| 2012/0197271 A1 | 8/2012 | Astorino et al. |
| 2012/0290002 A1 | 11/2012 | Astorino |
| 2012/0296345 A1 | 11/2012 | Wack et al. |
| 2013/0023928 A1 | 1/2013 | Dreyfuss |
| 2013/0023929 A1 | 1/2013 | Sulllivan et al. |
| 2013/0096612 A1 | 4/2013 | Zajac et al. |

FOREIGN PATENT DOCUMENTS

| | | |
|---|---|---|
| EP | 0440991 A1 | 8/1991 |
| EP | 1108401 A1 | 6/2001 |
| EP | 1707127 A1 | 10/2006 |
| EP | 2238944 A2 | 10/2010 |
| EP | 2263608 A1 | 12/2010 |
| EP | 2311383 A1 | 4/2011 |
| WO | 02/091959 A1 | 11/2002 |
| WO | 2007/002561 A1 | 1/2007 |
| WO | 2008/091690 A1 | 7/2008 |

* cited by examiner

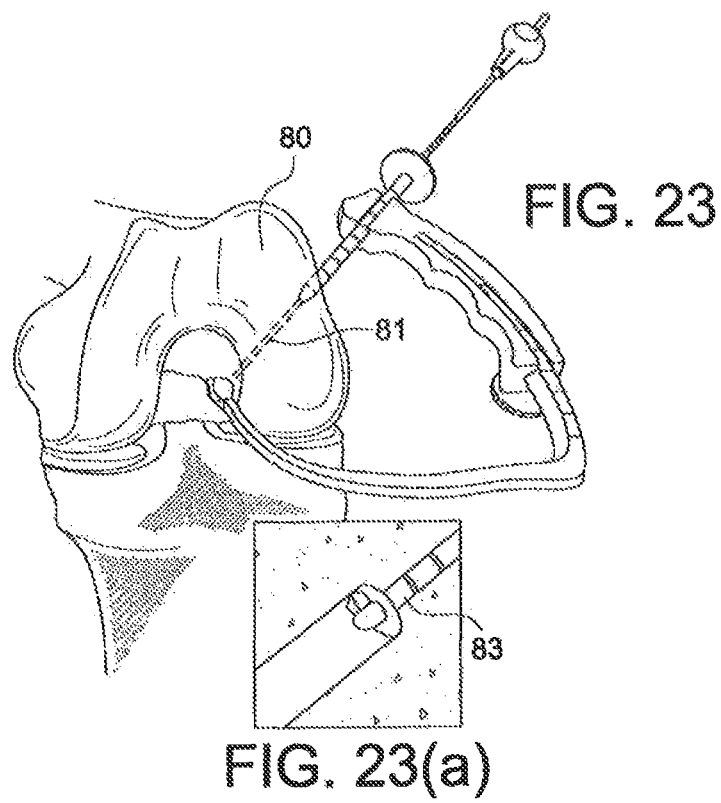
FIG. 23
FIG. 23(a)
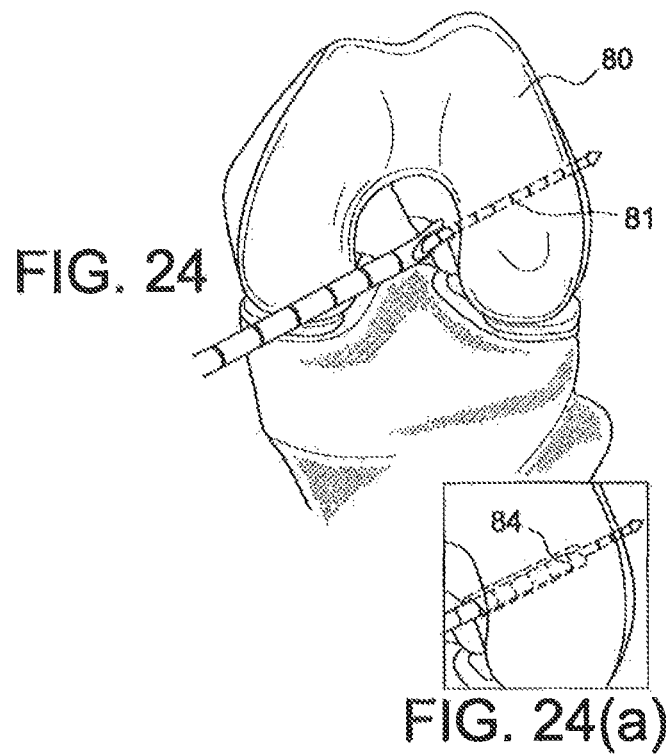
FIG. 24
FIG. 24(a)

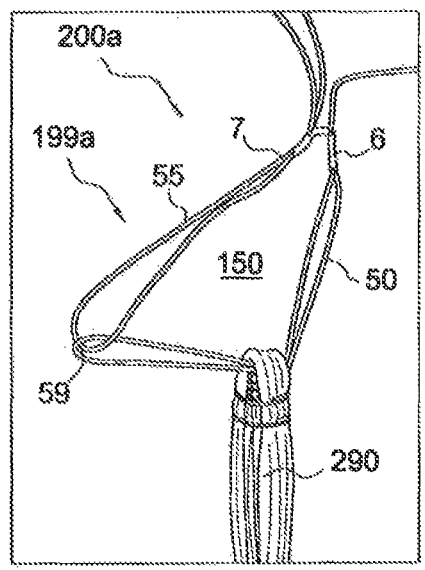
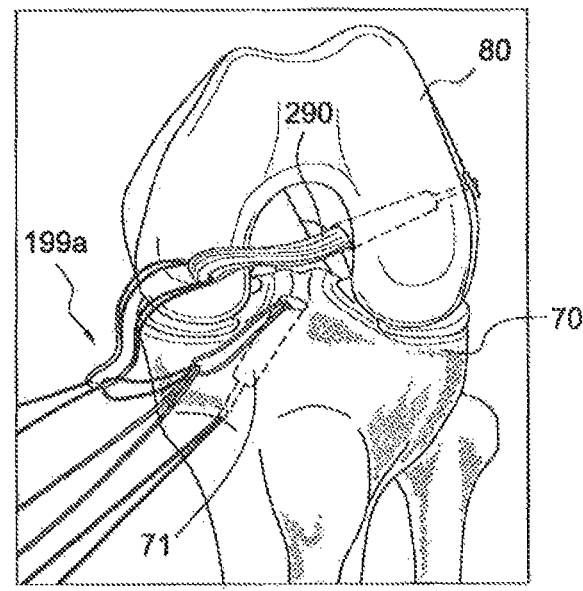
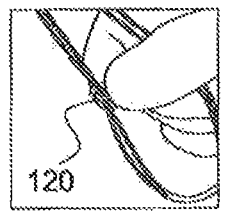
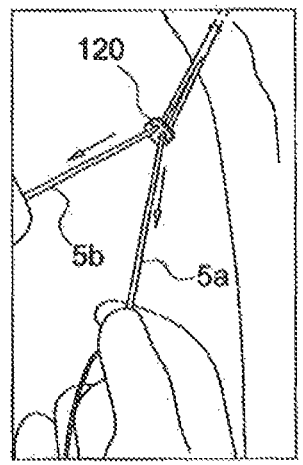
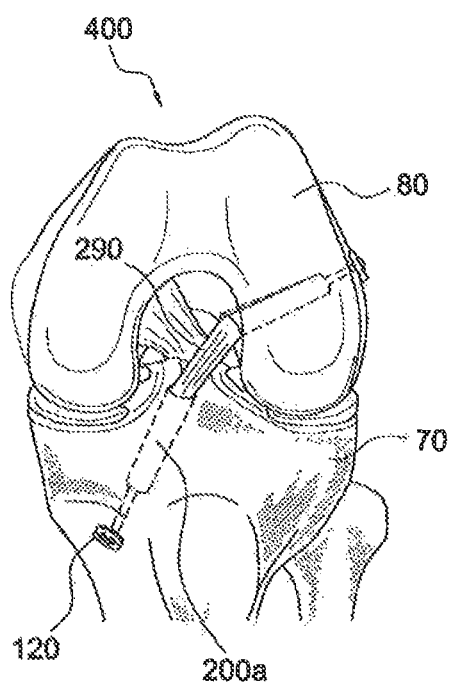

ADJUSTABLE SELF-LOCKING LOOP CONSTRUCTS FOR TISSUE REPAIRS AND RECONSTRUCTIONS

CROSS-REFERENCE TO RELATED APPLICATIONS

This is a divisional of U.S. patent application Ser. No. 13/647,549, filed Oct. 9, 2012, which claims priority to U.S. Provisional Application No. 61/546,305, filed Oct. 12, 2011, the entire disclosures of which are incorporated by reference herein.

FIELD OF THE INVENTION

The present invention relates to the field of surgery and, more particularly, to tissue repairs and reconstruction techniques, and associated fixation and reconstruction devices.

BACKGROUND OF THE INVENTION

Adjustable suture-button constructs and associated techniques for fixation of a tendon or ligament, such as an ACL, are disclosed in U.S. Patent Application Publication Nos. 2010/0256677 and 2010/0268273, the disclosures of which are incorporated by reference herein in their entirety.

Securing a bone block with cortical buttons and loop fixation devices (such as adjustable suture-button constructs) is difficult as a bone-tendon-bone (BTB) graft has two distinct ends and cannot be folded through a loop like a soft tissue graft. It would be desirable to provide adjustable suture-button constructs and techniques for soft tissue repairs (such as BTB ACL reconstruction) that easily secure a bone block to cortical bone, in a way that minimizes material removal from the bone block, minimizes compressive force to the bone block and secures a bone block to cortical bone without the damaging compressive forces, while promoting easy self-locking adjustability.

SUMMARY OF THE INVENTION

The present invention provides methods and reconstruction systems for knotless reconstruction of tissue that securely fixate the tissue to bone. The reconstruction system comprises an adjustable, self-locking knotless tensionable construct attached to tissue, for further insertion into a bone tunnel or socket. The tensionable construct (fixation device) is adjustable in length and allows the surgeon the ability to customize the device to each patient and seat the graft against the wall of the bone tunnel or socket. The adjustments are self-locking and the fixation device minimizes the compressive forces on the bone block.

These and other features and advantages of the present invention will become apparent from the following description of the invention that is provided in connection with the accompanying drawings and illustrated embodiments of the invention.

BRIEF DESCRIPTION OF THE DRAWINGS

FIGS. 19-30 illustrate steps of a method of ACL reconstruction with the integrated system of FIG. 18 (BTB TightRopeC).

FIGS. 31-40 illustrate steps of a method of ACL reconstruction with another integrated system (surgical construct) of the present invention (a soft tissue graft attached to a self-locking, adjustable tensionable construct without a button).

DETAILED DESCRIPTION OF THE INVENTION

Figure 1:
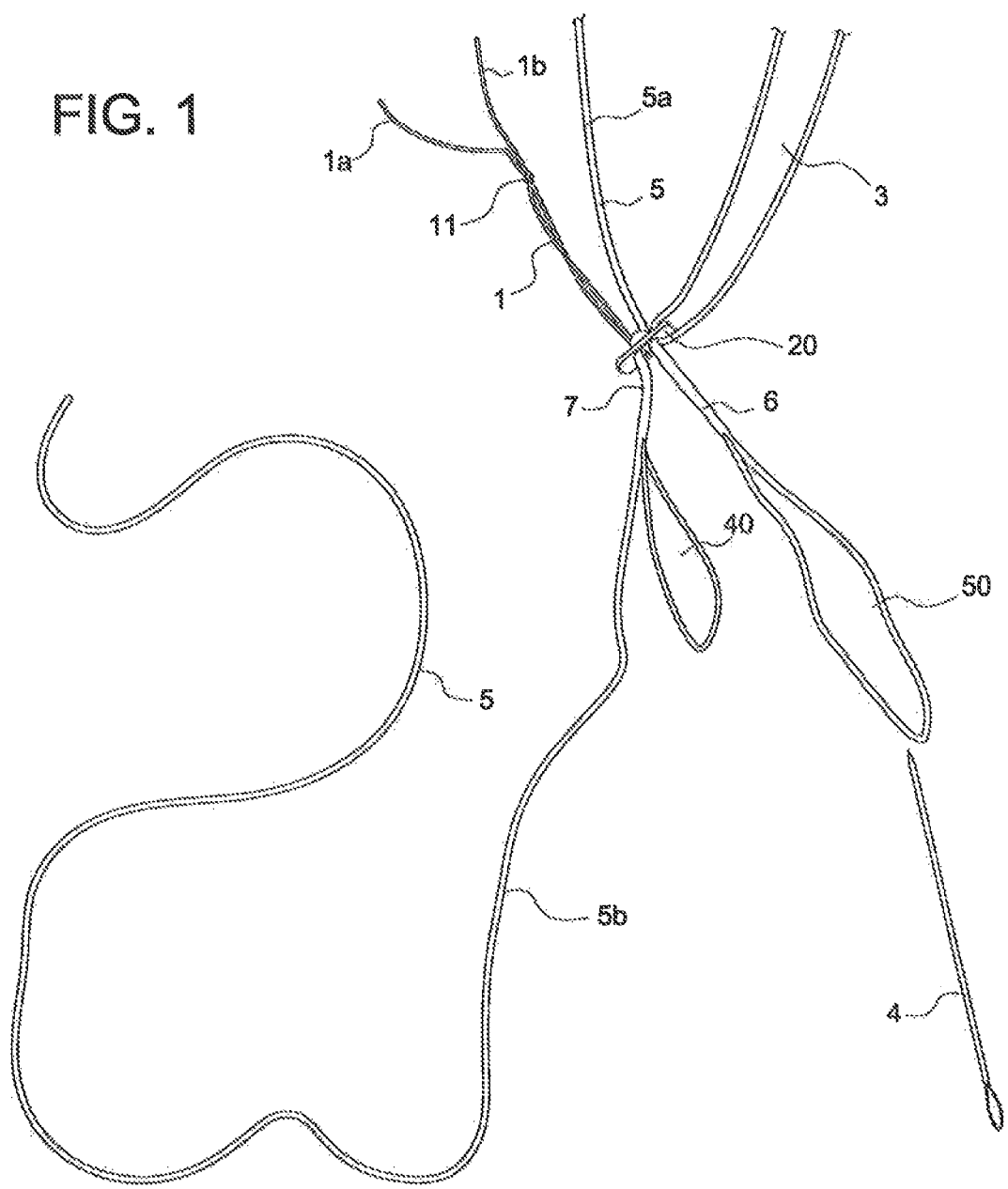
FIG. 1 illustrates an exemplary knotless, self-locking, adjustable button/loop construct (pre-assembled tensionable construct) of the present invention.

The present invention provides surgical constructs, systems and techniques for knotless tissue repairs and fixations. The surgical constructs comprise a tensionable construct with an adjustable, self-locking knotless flexible closed loop connected to tissue (such as soft tissue, graft, tendon, ligament, synthetic material, biological material, bone, or combinations of such materials, among others). The tissue may be directly looped over the flexible adjustable loop, or the flexible adjustable loop may be passed through tissue, for insertion and fixation into a bone tunnel or socket. The surgical constructs may also comprise a splicing device (a shuttle/pull device) adjacent the flexible, adjustable loop. The splicing device may be a suture passing instrument such as a closed loop, a FiberLink™, a nitinol wire loop, a needle pre-inserted into a splice area, or any splicing device that aids in the formation of a final splice in the adjustable loop). The tensionable construct may optionally include a fixation device (for example, a button) securely attached to the adjustable loop. The splicing device (suture passing instrument or shuttle/pull device) aids in the formation of the final splice of the adjustable, self-locking knotless flexible closed loop. The tensionable construct is adjustable in length and allows the surgeon the ability to customize the device to each patient and seat the graft against the wall of the bone tunnel or socket. The adjustments are self-locking and the fixation device (implant) minimizes the compressive forces on the bone block.

According to an exemplary embodiment, the tensionable construct is provided as a pre-assembled or pre-packaged construct on an assembly board upon which an adjustable flexible closed loop, a shuttle/pull device, a passing suture for fixation device, and a needle are mounted (in a kit, for example) and assembly instructions are provided. The pre-assembled tensionable construct may be assembled with BTB grafts or other tissue grafts (such as a ligament graft like an autograft, allograft or artificial graft), at the time of surgery, to form integrated systems for tissue repairs and reconstructions. During the assembly, the self-locking flexible adjustable closed loop is provided around tissue graft (for example, around a BTB block or a soft tissue strand) or through tissue. If a BTB construct is employed, the self-locking adjustable loop is provided around the BTB bone block without forming any knots or any crossing of the loop strands between the top of the bone block and the button. This minimizes the compressive forces on the bone block which, in turn, leads to a stronger reconstruction. The absence of any knots also limits the chances of the knot tightening down and restricting the adjustability of the implant.

If an exemplary BTB graft is employed, the tensionable construct is assembled with the BTB graft by passing the self-locking adjustable loop of the tensionable construct through a hole in the bone block, and then passing the free strand of the construct through the looped end of the construct and through the loop of the shuttle/pull device (provided in the form of a splice loop of fixed diameter, for example). The flexible strand and the shuttle/pull device attached to it allow the formation of a final splice for the adjustable loop. The shuttle/pull device is provided within the strand (inside of the strand) and forms the final splice subsequent to the insertion of the self-locking adjustable loop through the hole in the bone block. The shuttle/pull device is removed subsequent to the formation of the final splice, and is not part of the final implantable construct (final assembled integrated system).

The integrated systems of the present invention allow formation of the final fixation device with a knotless self-locking mechanism that allows the user (for example, the surgeon) to control the tension of the strand on the tissue to be attached to bone.

At least one of the flexible strand and the splicing device (shuttle/pull device) may be made of any known suture material, such as ultrahigh molecular weight poly ethylene (UHMWPE) or the FiberWire suture (disclosed in U.S. Pat. No. 6,716,234 which is hereby incorporated by reference in its entirety). Typically the suture will be UHWMPE suture without a core to permit ease of splicing. The shuttle/pull device may be a suture passing instrument such as a splicing loop (for example, a loop of a flexible strand, or a FiberLink™ or a Nitinol loop) or a needle pre-inserted into the splice area or any device that allows formation of a final splice in the adjustable closed loop of the tensionable construct.

The present invention also provides methods of fixation of bone to bone, or soft tissue to bone. An exemplary method of the present invention comprises the steps of: (i) providing a bone tunnel; (ii) providing a button/graft construct including a button and a loop of flexible material having an adjustable length, in the vicinity of the bone tunnel; (iii) attaching tissue to the button/graft construct by looping the tissue (graft) over the adjustable loop or, alternatively, by passing the loop of flexible material through the tissue (graft); (iv) advancing the button/graft construct with the attached tissue through the bone tunnel; and (v) securing the tissue within the bone tunnel by adjusting the length of the adjustable loop.

The present invention also provides methods of tissue repair which do not require tying of knots and allow adjustment of both the tension of the suture and the location of the tissue with respect to the bone. An exemplary method of the present invention comprises inter alia the steps of: (i) providing a pre-assembled construct including an adjustable, self-locking knotless flexible closed loop with at least one splice in a flexible strand, the flexible closed loop being adjacent a shuttle/pull device (a splicing device or a suture passing instrument); (ii) assembling the pre-assembled construct with a tissue graft (BTB or other soft tissue graft) by passing the adjustable, self-locking knotless flexible closed loop through or around tissue, and then forming a final splice in the adjustable, self-locking knotless flexible closed loop with the shuttle/pull device to obtain a final implantable construct; (iii) securing the final implantable construct into a bone tunnel/socket; and (iv) pulling on the flexible strand to allow the tissue graft to achieve the desired location relative to the bone, and to allow proper tensioning of the final construct.

Figure 1A:
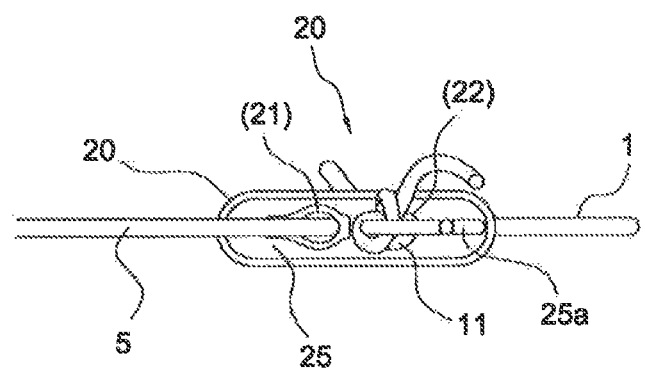
FIG. 1*a* illustrates a top view of the button of the tensionable construct of FIG. 1.
Figure 17:
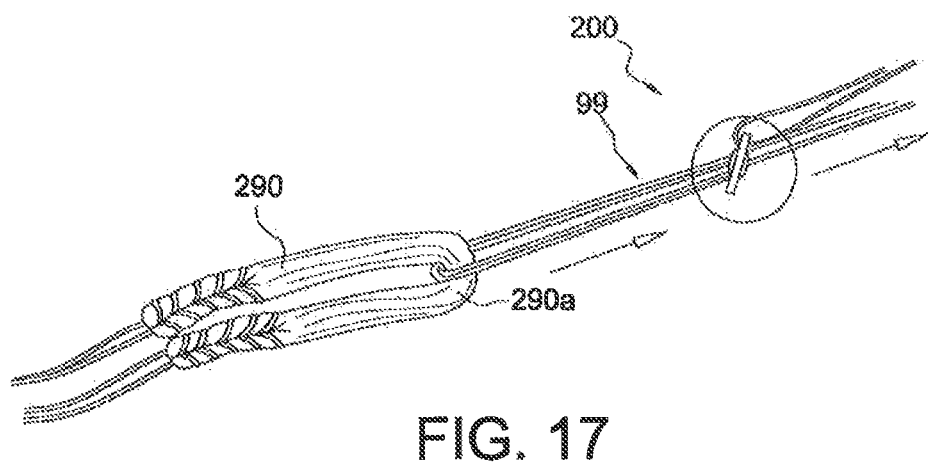
FIG. 17 illustrates a surgical construct (implantable integrated system or surgical system) according to an exemplary embodiment of the present invention (with the self-locking, adjustable button/loop construct of FIG. 6 attached to an exemplary soft tissue graft).
Figure 18:
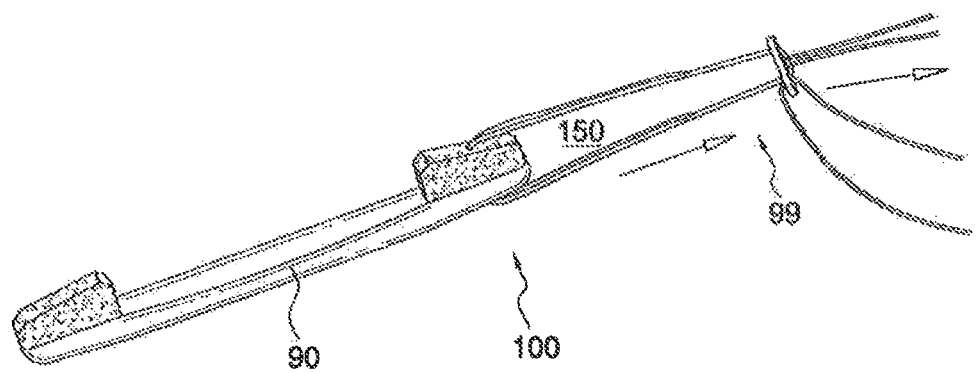
FIG. 18 illustrates a surgical construct (integrated system or a BTB TightRope®) according to another exemplary embodiment of the present invention (the self-locking, adjustable button/loop construct of FIG. 6 attached to an exemplary BTB graft).

Referring now to the drawings, where like elements are designated by like reference numerals, FIG. 1 illustrates an exemplary tensionable construct 99 (ACL TightRope® 99) of the present invention employed for the formation of surgical integrated systems 100, 200, 200a (FIGS. 17, 18 and 35, respectively). In the particular exemplary embodiment illustrated in FIG. 1, tensionable construct 99 is formed of a knotless, closed, adjustable loop 50 formed of a flexible strand 5 or flexible material 5 and a shuttle/pull device 40 (a suture passing instrument or a splicing device such as a fixed loop 40, a FiberLink™ 40, a nitinol loop 40 or a needle 40, for example) attached to the flexible strand 5 (i.e., pre-loaded on the flexible strand). Optionally, tensionable construct 99 may include a fixation device 20 (for example, a button 20). A top view of an exemplary fixation device 20 is shown in FIG. 1a. Device 20 has a body 25 with an oblong configuration (when viewed along a longitudinal axis 25a of the device) and a plurality of holes, a tear drop hole 21 and a round hole 22 extending along the longitudinal axis 25a.

As detailed below, the knotless, closed, adjustable loop 50 is formed by splicing an end 5a of flexible material 5 (for example, braided high strength (UHMWPE) suture strand 5 provided in a predetermined color, for example, white) to form splice 6. The splice 6 and loop 50 are secured to button 20 by sliding the button over the non-spliced strand 5b and passing the strand 5b through both button holes 21, 22 so that the splice 6 will rest on (abut) the thickness of the button 20.

The knotless, closed, adjustable loop 50 has an adjustable perimeter and length, and is capable of adjusting tension. Details for the formation of adjustable closed loop constructs (similar to the loop 50) are set forth, for example, in U.S. Patent Application Publication Nos. 2010/025667 and 2010/0268273, the disclosures of which are incorporated herein in their entirety.

Shuttle/pull device 40 (splicing device 40) of the tensionable construct 99 may be any suture passing device or splicing device configured to create a final splice in the knotless, closed, adjustable loop 50 after attachment to tissue to be reconstructed/repaired, and as detailed below. Shuttle/pull device 40 may be a suture passing instrument in the form of a pre-loaded flexible strand, a loop with a fixed perimeter, a FiberLink™, a nitinol wire loop or a needle pre-attached to the flexible strand forming the knotless, closed, adjustable loop 50, for example.

In an exemplary embodiment, shuttle/pull device 40 is a fixed closed loop with a fixed length and perimeter (i.e., non-adjustable). Fixed loop 40 may be formed by splicing another flexible strand 1 (for example, a #2 FiberWire® suture 1 provided in a predetermined color, for example, blue) through strand 5b by first folding the blue strand and then passing both free ends 1a, 1b of the blue strand through the non-spliced strand 5b to form loop 40, eyesplice 7 and loop section 1c below eyesplice 7. Ends 1a, 1b are tied in a static knot 11.

Figure 6:
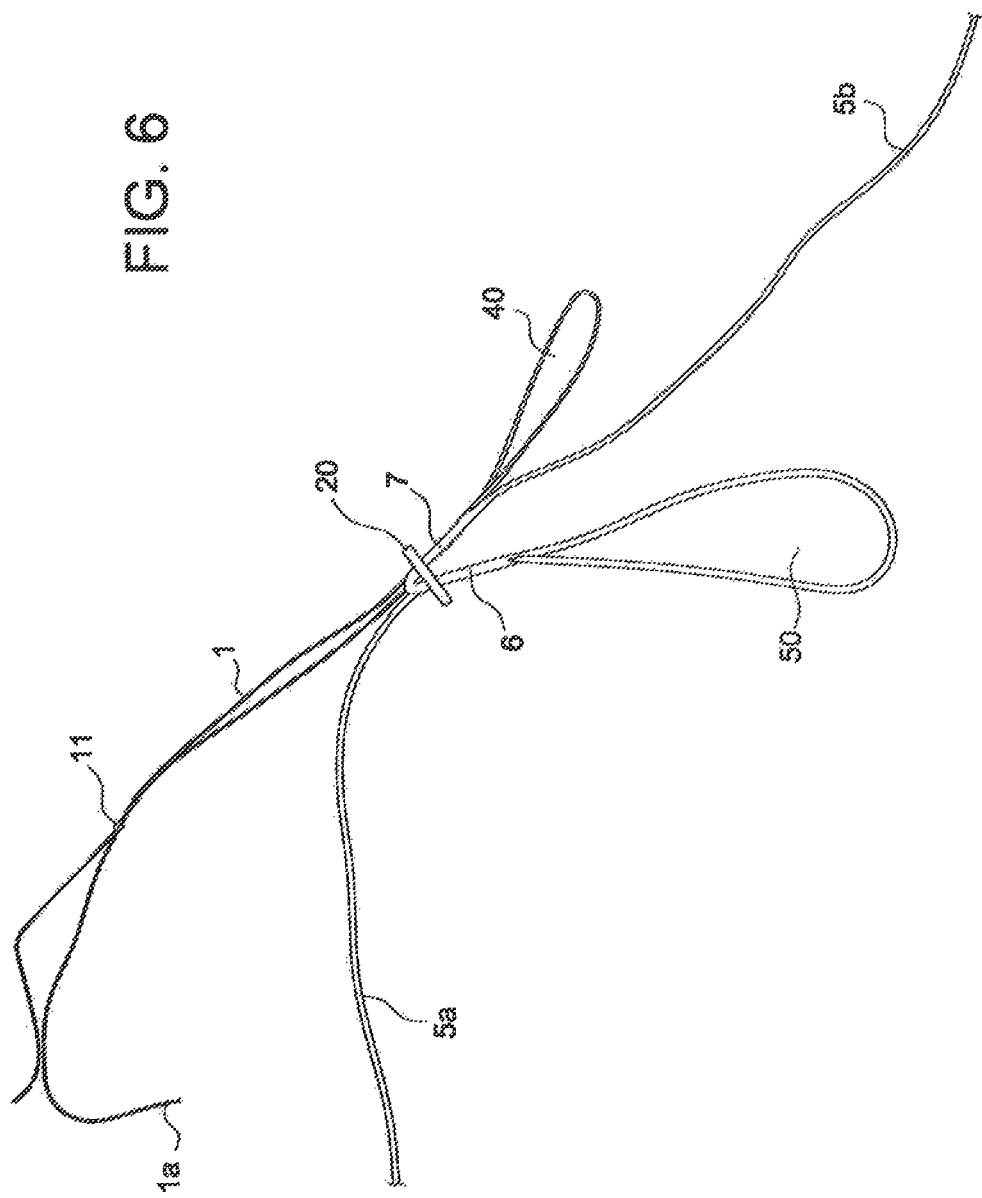

FIG. 1 also depicts a passing suture 3 (for example, a #5 FiberWire® suture) for pulling the button 20 through a bone tunnel or socket (for example, the femoral tunnel). Like the shuttle/pull device 40, the passing suture 3 is removed at the end of the implantation of the final construct. Also shown in FIG. 1 a straight needle 4 is attached to adjustable, knotless suture loop 50 for passing the construct (the implant) through a graft, as detailed below. Another illustration of the adjustable, knotless button/loop construct 99 of the present invention is depicted in FIG. 6.

Figure 2:
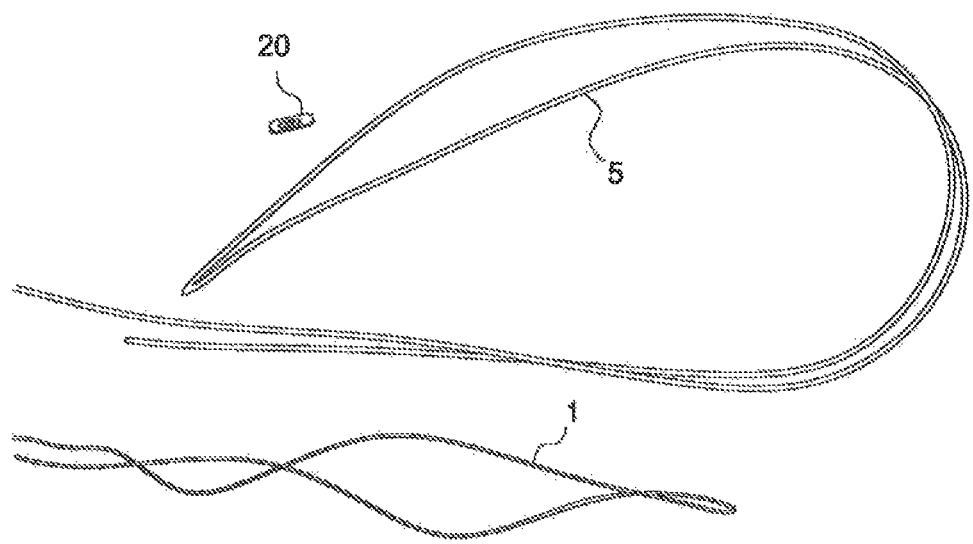
FIGS. 2-6 illustrate starting materials and steps of assembling the knotless, self-locking, adjustable button/loop construct of FIG. 1, according to an exemplary embodiment of the present invention.

FIG. 2 illustrates the button 20, flexible strand 5 (braid 5) and splicing suture 1, as starting materials used in configuring the construct 99.

FIGS. 3-6 illustrate exemplary steps of assembling the knotless, self-locking, adjustable button/loop construct 99 (tensionable construct 99).

Figure 3:
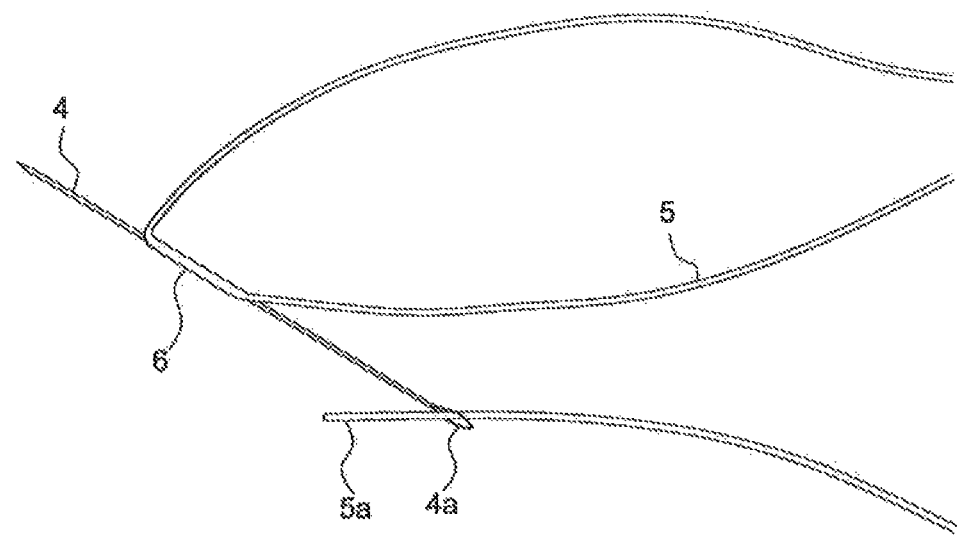

FIG. 3 (creating eyesplice 6 and adjustable, closed loop 50): Step 1: start with a flexible strand 5 (for example, a white braided suture 5 such as a UHMWPE braid 5 of about 40-50 inches); fold the braid at midpoint to create two equal length braid strands 5a, 5b.

Step 2: create an eyesplice 6 on one of the braid strands (for example, on strand 5a) by passing a blunt tip needle 4 through the center of the braid 5 and carrying the end 5a of the braid 5 through with it, in the nitinol loop 4a of the needle 4. The splice 6 should travel for a distance of about 16-18 mm through the braid, towards the midpoint created in step 1 to form adjustable, closed loop 50. Reduce the eyesplice loop 50 to about 80 mm.

Figure 4:
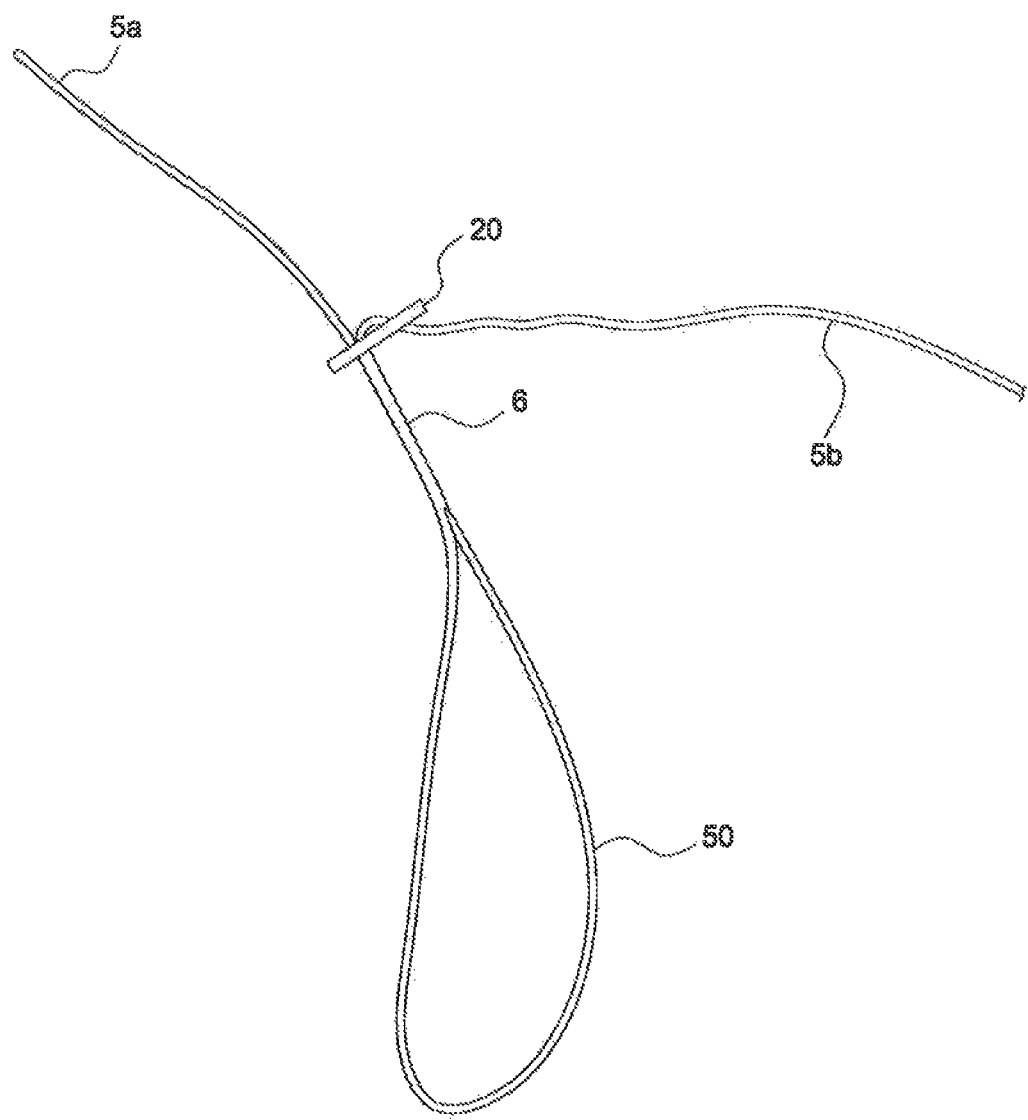

FIG. 4 (positioning the button 20): Step 3: slide a button 20 over the non-spliced strand 5b passing the strand through both button holes 21, 22 leading with the full round hole 22 of the button. Pass the free strand end 5a that results from the eyesplice 6 through the full round hole 22 and position the button 20 such that the exit point of the eyesplice 6 is resting within the thickness of the button 20.

Figure 5:
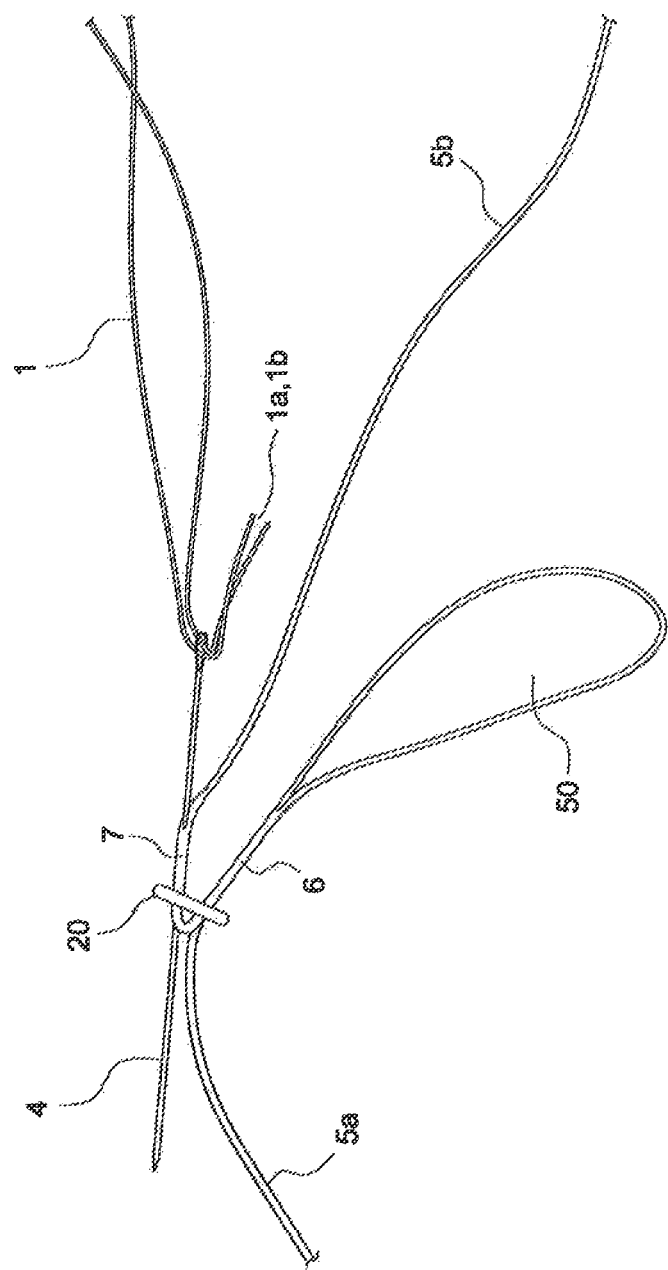

FIG. 5 (creating the second eyesplice 7 and the splicing loop 40): Step 4: prepare an eyesplice 7 in the same manner as Step 2 by employing another flexible strand 1 with two ends 1a, 1b (for example, a #2 blue suture braid 1). Fold the #2 blue braid 1 at the midpoint and pass both free ends 1a, 1b of the blue braid through the non-spliced strand 5b to form the second eyesplice 7.

FIG. 6 (construct assembly): Step 5: position the blue braid and tie the two free ends 1a, 1b into a simple overhand knot 11 above the button 20 to form splicing loop 40 (with a fixed perimeter), and loop end 1c.

Step 6: place a passing suture 3 (for example, a #5 FiberWire® suture, not shown) through the tear drop button hole 21 and position the passing suture 3 so that the strands are about equal length. The passing suture 3 will pull/pass the button 20 through the bone (femur or tibia).

Step 7: crimp the nitinol wire around a strand section 5c of adjustable loop 50 of the white braid; assemble the end of the nitinol wire into the needle capturing the white braid.

The pre-assembled construct (tensionable construct 99) is then provided to medical personnel in the OR (for example, surgeon) who then completes the final assembly to create the final implantable construct with the graft. The graft may be a BTB graft or any other soft tissue grafts (for example, a soft tissue graft that cannot be folded over the adjustable, knotless loop) or a ligament, tendon graft or a synthetic graft.

According to additional embodiments, just the loop construct (without fixation device/button 20) is provided to the surgeon. This embodiment could be used for soft tissue grafts that cannot be folded over the loop. In this "no button/loop assembly," the implantation is conducted with an attachable button (as detailed below with reference to FIGS. 31-40).

During the final assembly by the surgeon, the splicing loop 40 is removed after completing the splice. The passing suture 3 is also removed after the button 20 is implanted.

Reference is now made to FIGS. 7-16 which illustrate subsequent, exemplary steps of a method of assembling (attaching) the tensionable construct 99 to tissue (for example, soft tissue or BTB graft) to be repaired and/or reconstructed. Tensionable construct 99 is provided as a pre-assembled construct that includes a suture passing device 40 (splicing loop) that aids in creating the final splice for the adjustable loop. As detailed below, the suture passing device may have an exemplary loop configuration and it is not part of the final assembled construct that is implanted; suture passing device 40 is just an aid for the final assembly and for the formation of the final splice (and spliced loop) of the assembly. The suture passing device 40 is not limited to a flexible strand or a suture, but it could be a needle pre-inserted into the splice area or a nitinol wire loop, among others.

Details on assembling tissue 90 with the tensionable construct 99 to obtain integrated construct 100 of the present invention are set forth below with reference to FIGS. 7-16. The integrated construct 100 is a surgical implantable system consisting of tensionable construct 99 provided with knotless, adjustable loop 50 with a suture splicing device 40 attached to the knotless, adjustable loop 50 and tissue 90. During the final assembly by the surgeon, the suture passing device 40 (splicing loop 40) is removed after completing the splice and the formation of final "closed loop" 150. The passing suture 3 is also removed after the button 20 is implanted.

The embodiments detailed below will be explained, for simplicity, with reference to tissue 90 as being an exemplary BTB graft 90; however, the invention is not limited to this exemplary embodiment and encompasses any tissue and/or tissue graft. BTB grafts and other soft tissue grafts are harvested and provided at the time of surgery so they cannot be assembled by the manufacturer with the fixation device. The partially-assembled construct 99 (tensionable construct 99) is attached to the graft by the surgeon, and during surgery, to complete the assembly of the final construct in the OR. The partially-assembled construct 99 (tensionable construct 99) may be attached to one or both ends of a BTB graft (for the femoral and tibial sides), as desired and depending on the particulars of each surgical repair.

Figure 7:
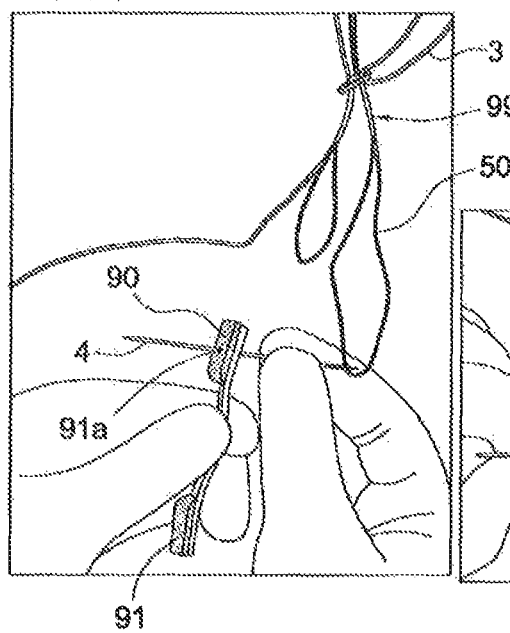
FIGS. 7-16 illustrate subsequent steps of attaching the self-locking, adjustable button/loop construct of FIG. 6 to an exemplary graft (a BTB graft) to form an integrated system (implantable surgical system) according to an exemplary embodiment of the present invention.
Figure 8:
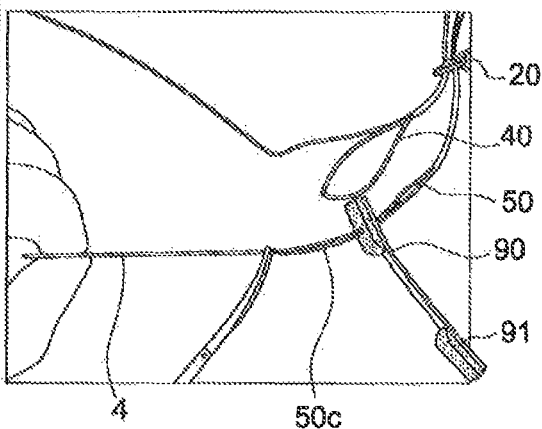

FIGS. 7 and 8: pass the straight needle 4 of Step 7 through a drill hole 91a formed within the bone block 91 of BTB graft 90 so that the loop 50 extends through the drill hole and a loop portion 50c is exposed. Once the implant 99 is passed, the needle 4 is cut off.

Figure 9:
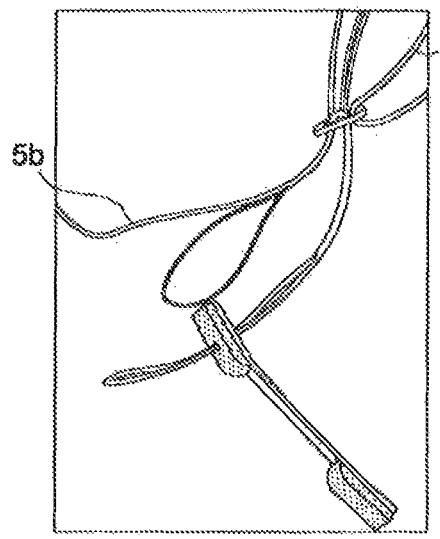
Figure 10:
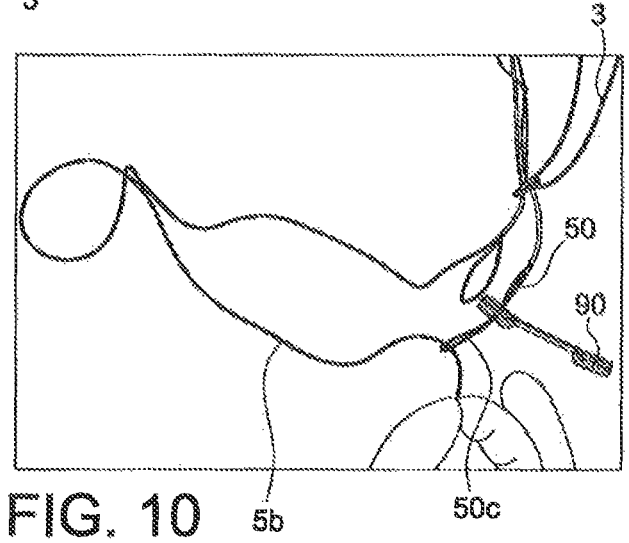

FIGS. 9 and 10: pass the free strand 5b of the implant 99 through looped portion 50c of the knotless, adjustable loop 50 (implant 50) that has been passed through the bone block 91.

Figure 11:
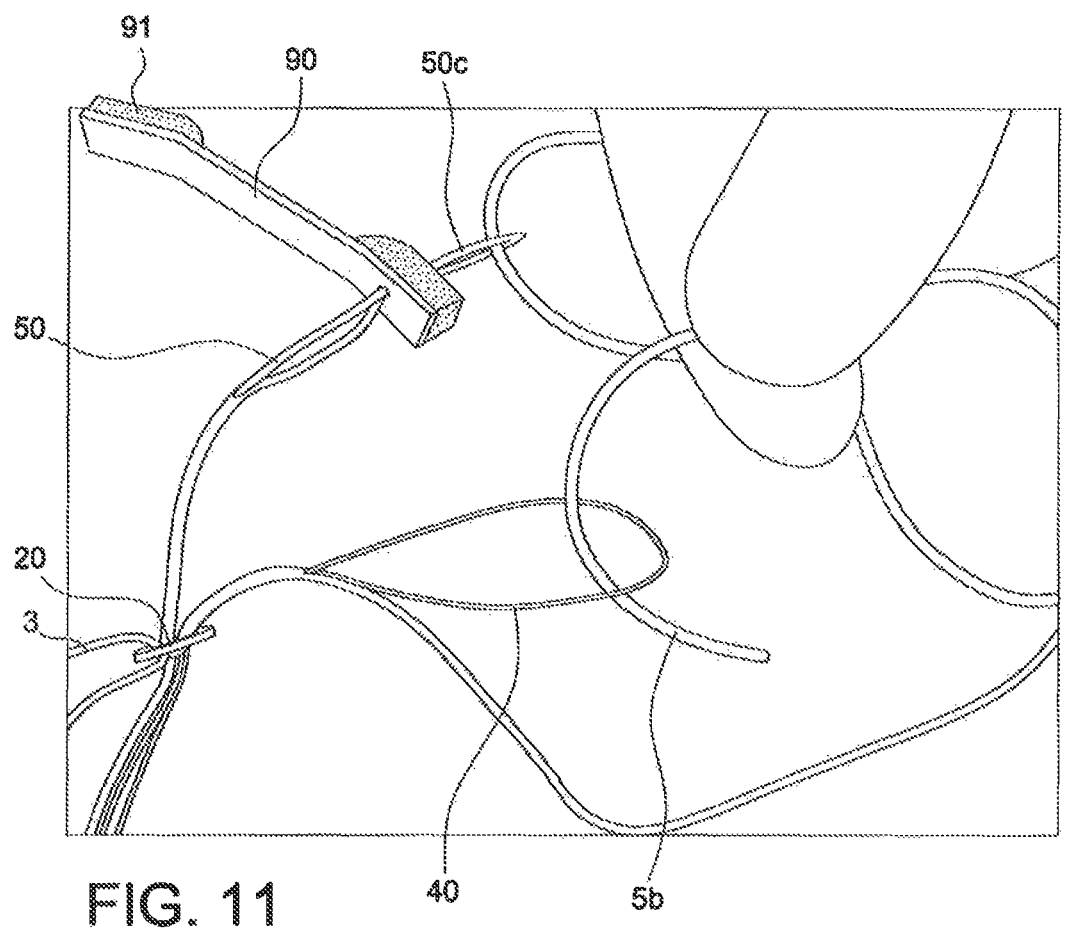

FIG. 11: pass the free strand 5b through the pre-loaded passing suture loop 40.

Figure 12:
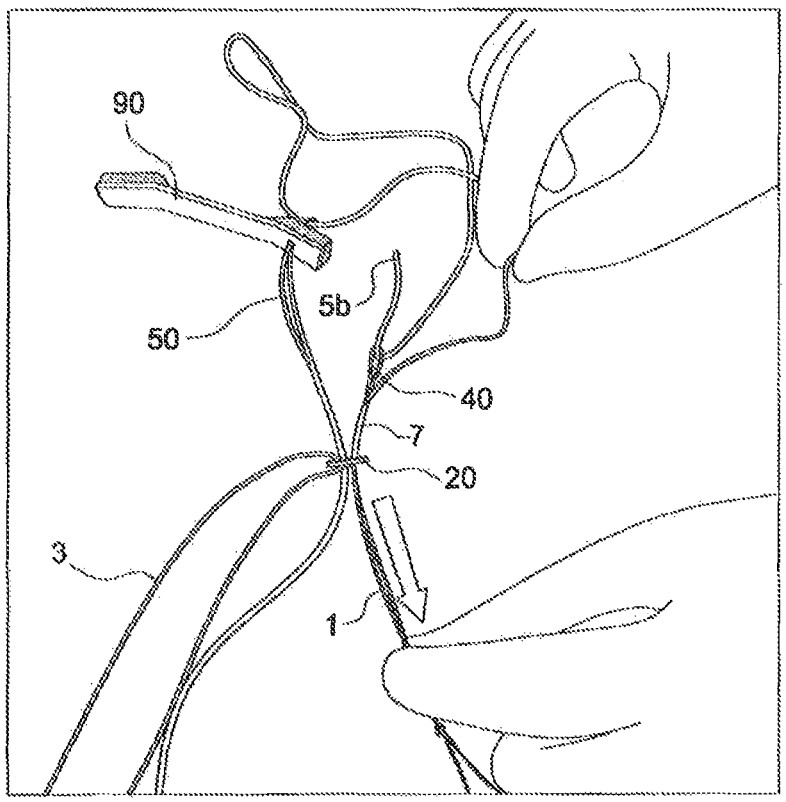
Figure 13:
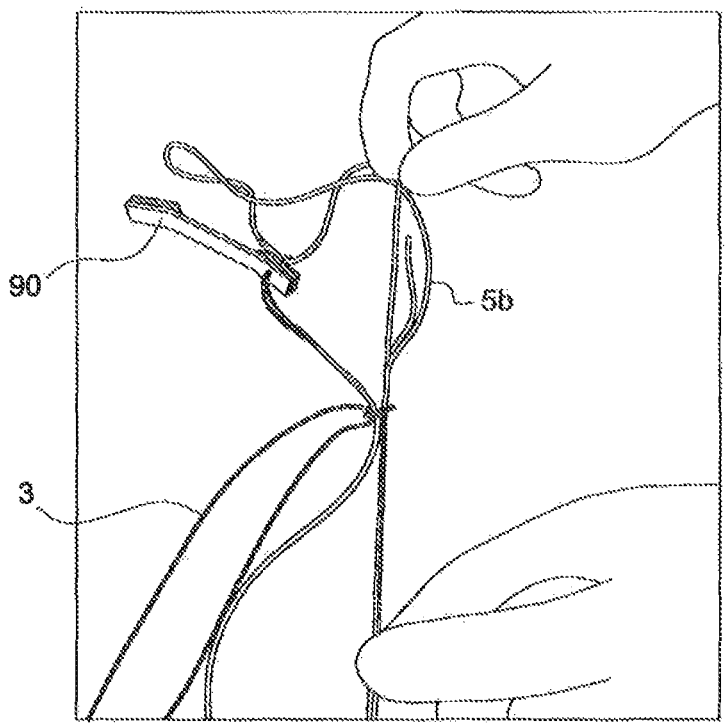

FIGS. 12 and 13: pull the tails 1a and 1b of the pre-loaded passing suture loop 40 through splice 7 of the implant 99 to advance the free strand 5b through the implant 99. The end of the free strand 5b is held tightly while pulling it through the implant 99.

Figure 14:
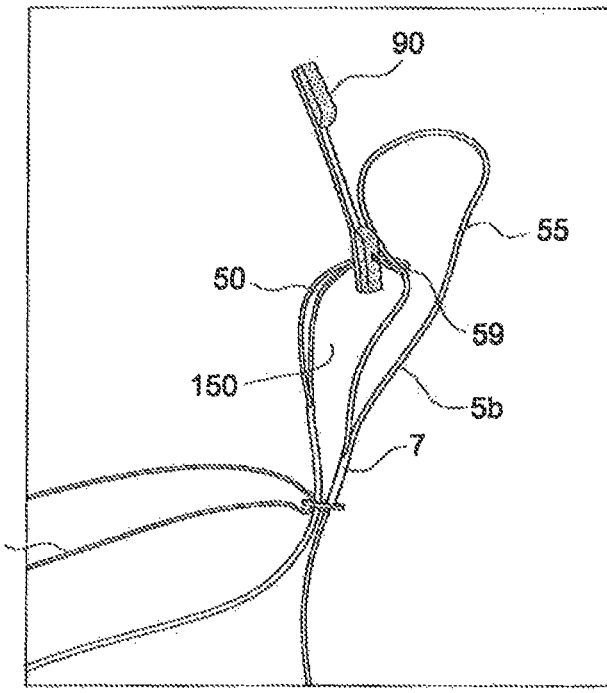

FIG. 14: the free strand 5b passes through the eyesplice 7, forming loop 55 which is interconnected (interlinked) with adjacent knotless, adjustable loop 50 through connecting region 59. The free strand 5b now becomes the shortening strand of the construct 99 (TightRope® 99).

Figure 15:
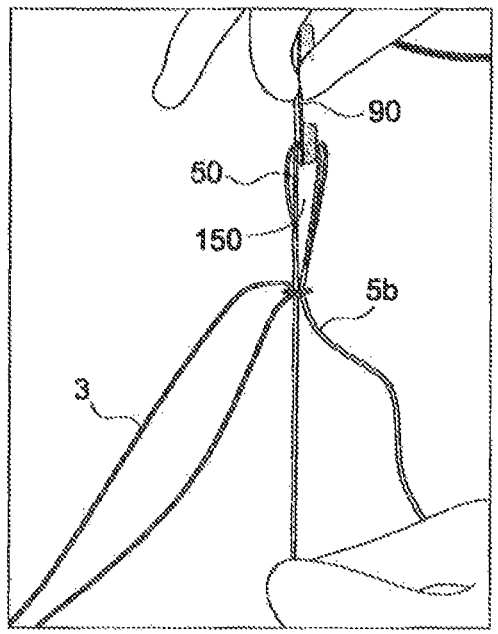

FIG. 15: even out the implant 99 by pulling the shortening strands until the implant 99 is symmetric (i.e., interconnecting region 59 of the two interconnected loops 50, 55 is within hole 91a of the bone block 91). Final closed loop 150 is formed by the two interconnecting loops 50, 55 and two splices 6, 7.

Figure 16:
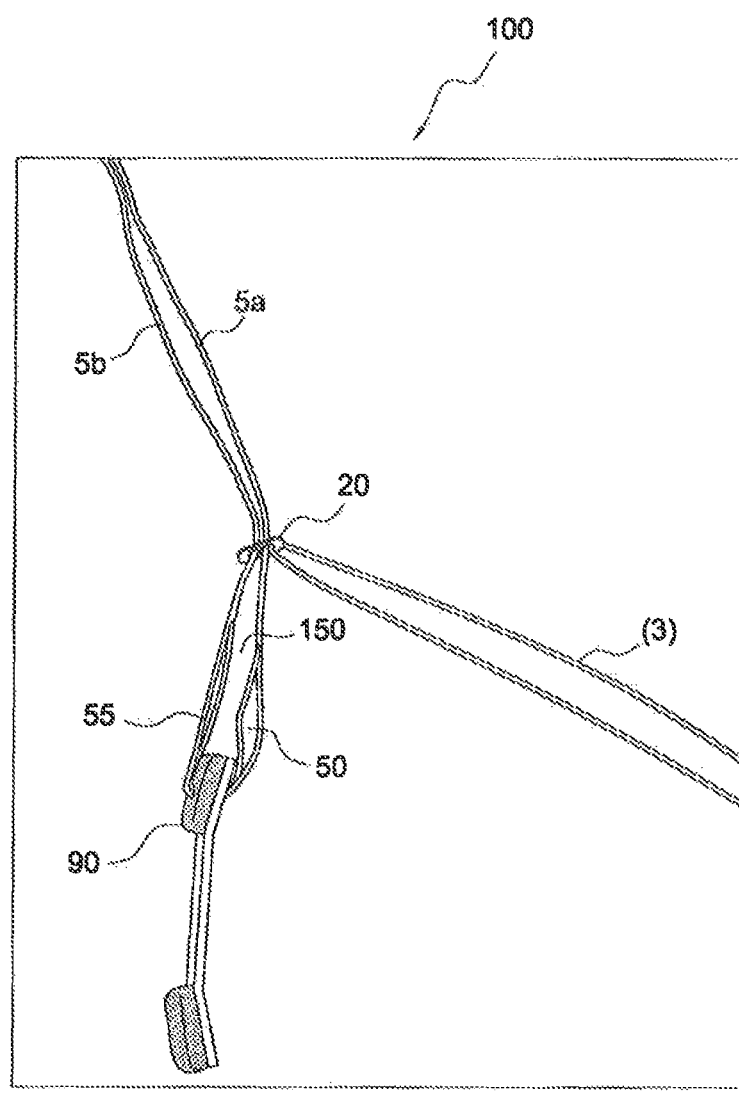

FIG. 16 shows the final construct 100 (integrated assembly 100) with the two shortening strands 5a, 5b of the TightRope® 99 and the two strands of #5 FiberWire® suture 3 for passing button 20. Closed loop 150 is attached to both the graft 90 and fixation device 20 (button 20).

FIGS. 17 and 18 illustrate two exemplary integrated systems 100, 200. Integrated system 100 (BTB TightRope® 100) includes tensionable construct 99 and BTB graft 90. Integrated system 200 (ACL TightRope® 200) includes tensionable construct 99 and soft tissue 290. Integrated system 200 (ACL TightRope® 200) is formed in a manner similar to that described above for the formation of integrated system 100, the difference being that the knotless adjustable loop 50 is passed not through tunnel 91 of the bone block 90 but rather passed around (and secured to) a mid portion 290a of folded soft tissue graft 290 (shown in FIG. 17, with the graft 290 being folded and looped over the interconnect region 59 formed by loops 50, 55).

FIGS. 19-30 illustrate steps of an ACL reconstruction with an exemplary BTB TightRope® 100 (integrated system 100) of the present invention. The simplicity and strength of the ACL TightRope® is used with bone-tendon ACL grafts. The BTB TightRope® (tensionable construct 99) offers the same adjustable, four-point locking system as the ACL TightRope® but allows placement through a small drill hole in the cortical bone block. The TightRope® button 20 facilitates dependable, cortical fixation and the adjustable loop 50 allows the graft to be pulled into the femoral socket as deep as needed for ideal graft tunnel-matching. The BTB TightRope® 99 also allows fixation of BTB grafts 90 into anatomic femoral sockets that can be difficult to reach with traditional interference screws.

Figure 41:
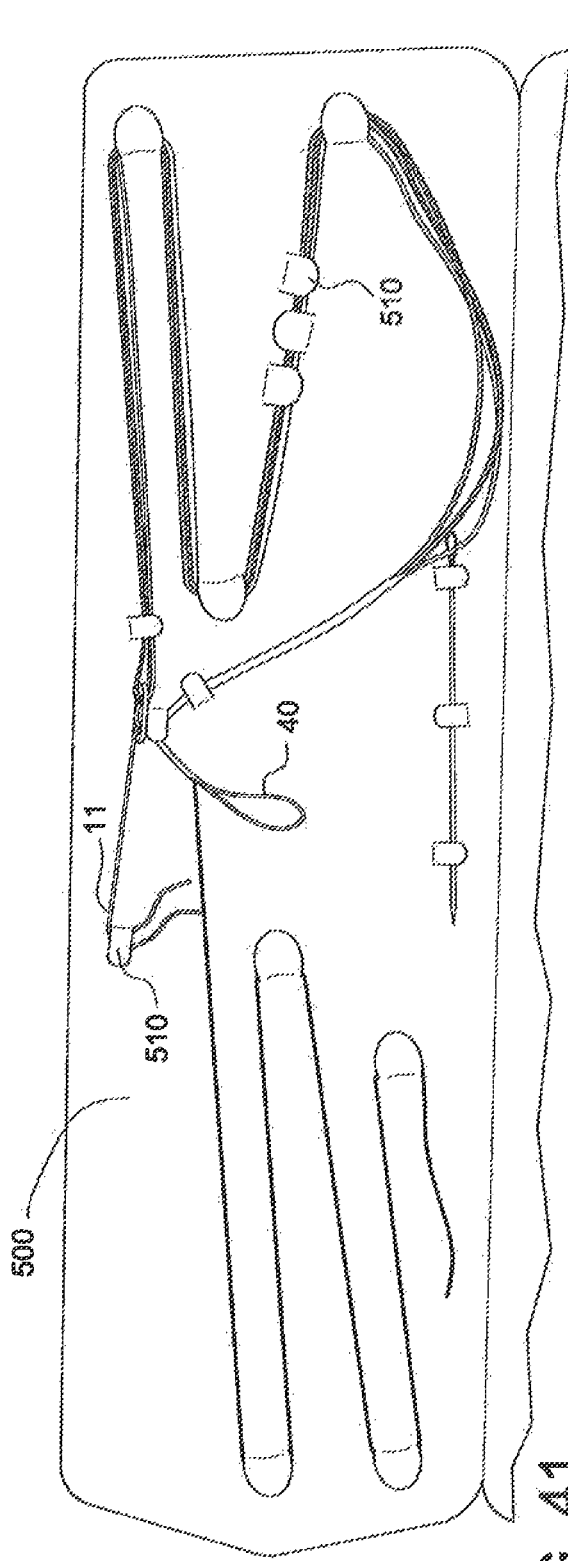
FIG. 41 illustrates an assembly board with a mounted self-locking, adjustable button/loop construct of the present invention used to assist in attaching a graft (for example, an exemplary BTB ACL graft).

For graft preparation and implant loading, use the BTB TightRope® for bone blocks of about 10 mm in diameter and about 20 mm in length. Use a 2 mm drill pin to place a hole about 10 mm from the end of the bone block, perpendicular to the cortical bone. The BTB TightRope® 99 is packaged in a special card to facilitate assembly (as shown in FIG. 41). Step-by-step instructions (FIG. 42) may be also included on the card.

Figures 19, 20:
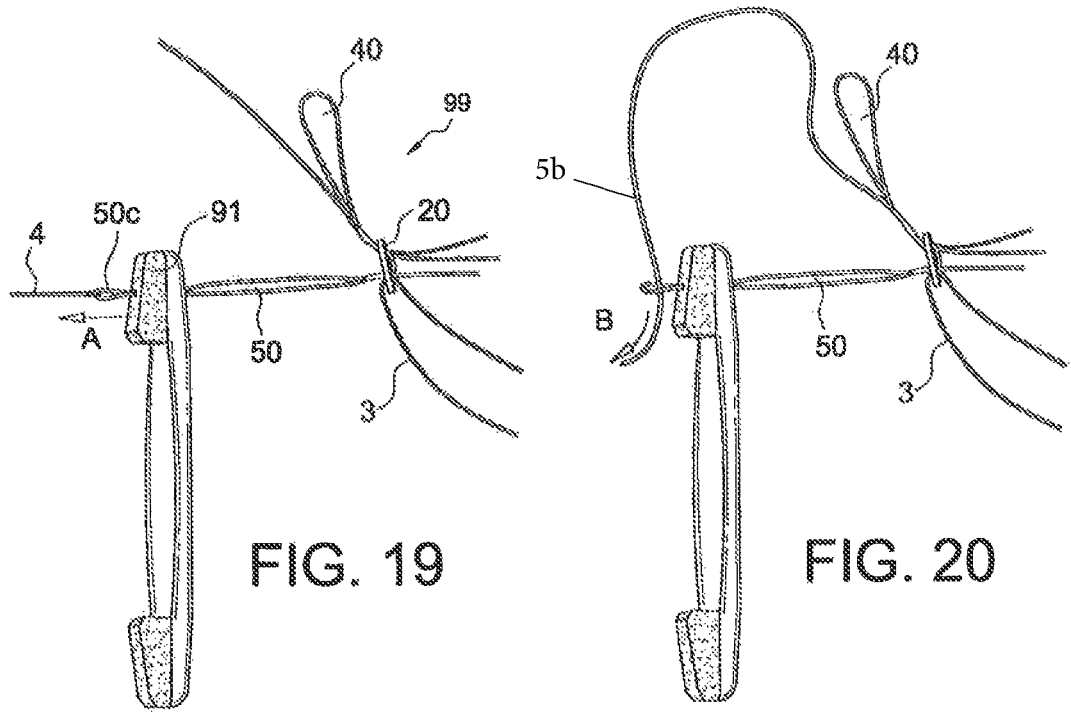

FIG. 19: Use the attached needle 4 to pass the looped limb 50 of the TightRope® 99 through the bone block 91 in the direction of arrow A. Once passed, cut the wire off the needle 4 and remove. Take care not to damage implant (loop 50) during cutting.

FIG. 20: Pass the straight limb 5b of the TightRope® 99 through the first loop 50c in the direction of arrow B.

Figures 21, 22:
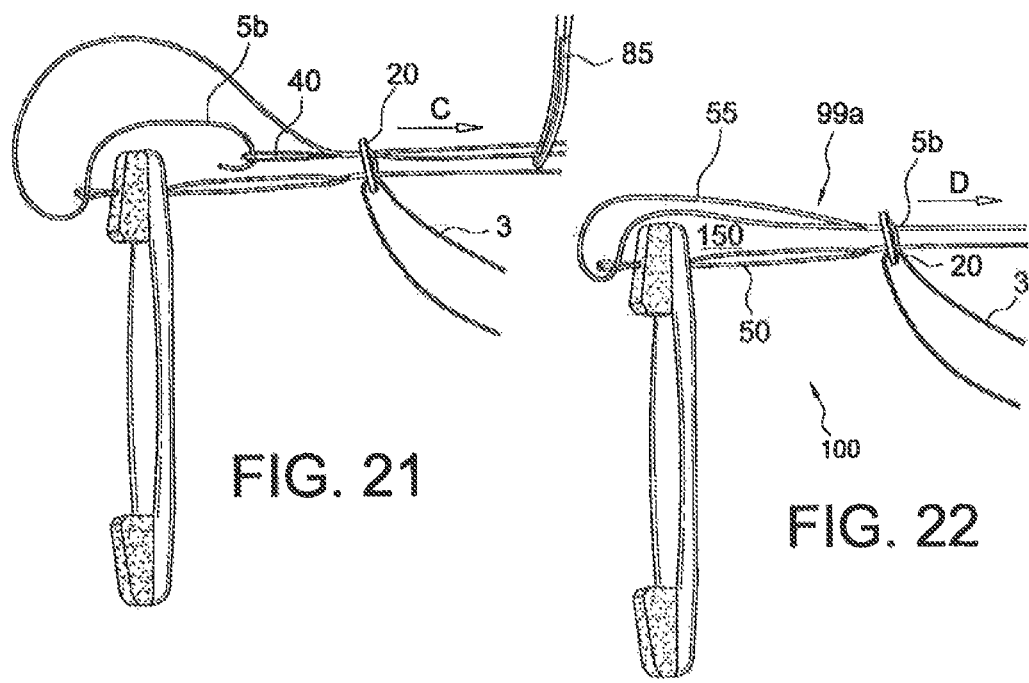

FIG. 21: Place 1 cm of the tip of the straight limb 5b into the blue passing suture loop 40 and fold over. Pull the tails of the passing suture loop to deliver the straight limb 5b through the suture splice 7 and button 20. Importantly, as the suture is passed through the splice (by pulling in the direction of arrow C), resistance will be encountered. A hemostat 85 may be used to pull the passing suture while holding firm counter tension on the straight suture.

FIG. 22: Pull on the newly created shortening strand to even up loop lengths before implantation (by pulling in the direction of arrow D) and to form final construct 100. Final integrated construct 100 includes tensionable construct 99a (i.e., without the splicing device 40) and BTB graft 90 attached to it. Closed loop 150 of tensionable construct 99a is attached to both the graft 90 and the fixation device 20. Splices 6, 7 of loops 50, 55 forming closed loop 150 abut the fixation device 20. Final integrated construct 100 is implanted into a bone tunnel or socket, as detailed below.

FIGS. 23 and 24: FEMORAL SOCKET PREPARATION—The femoral socket 81 can be prepared in femur 80 in a retrograde fashion using the FlipCutter® and the RetroConstruction™ Guide System, by a retrograde technique using an Arthrex FlipCutter®, disclosed in U.S. Patent Application Publication No. 2009/0275950. Alternatively, the socket may be drilled transtibially through the medial portal or in an antegrade fashion with a ACL TightRope® Drill Pin and Low Profile Reamers. In a Medial Portal Option, for medial portal and transtibial drilling, an Arthrex RetroButton® Drill Pin may be used. Note the intraosseous length during tunnel preparation and mark that distance on the ACL TightRope® RT implant. FIG. 23 shows the FlipCutter® Option employing a FlipCutter® 83. FIG. 24 shows the Medial Portal Option employing a drill/cutter 84.

Figure 25:
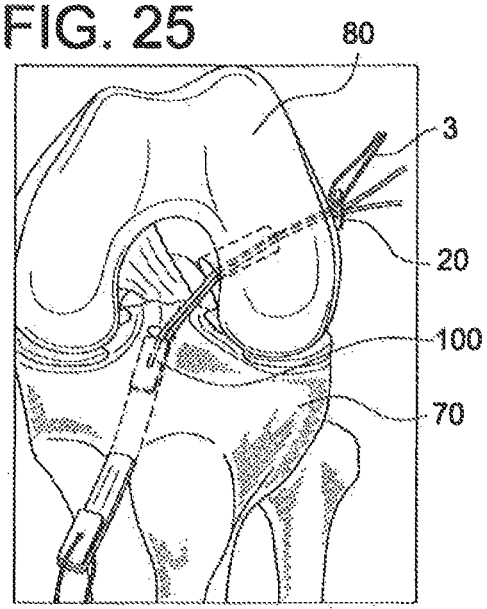

FIG. 25: Pass the blue passing suture 3 and white tensioning strands 50, 55 together through the femur 80. Pull even tension on both sets of sutures. Clamp sutures together and pull to advance button 20. Pull the button 20 through the femur 80. A line on the implant marked at the intraosseous length is helpful to signal that the button has exited the femur. The button 20 can also be viewed through the medial portal as it exits the femoral cortex. If tunnels are divergent, it may be helpful to use a probe through the lateral portal to facilitate implant and graft passage out of tibia 70 and into the femoral socket.

Figure 26:
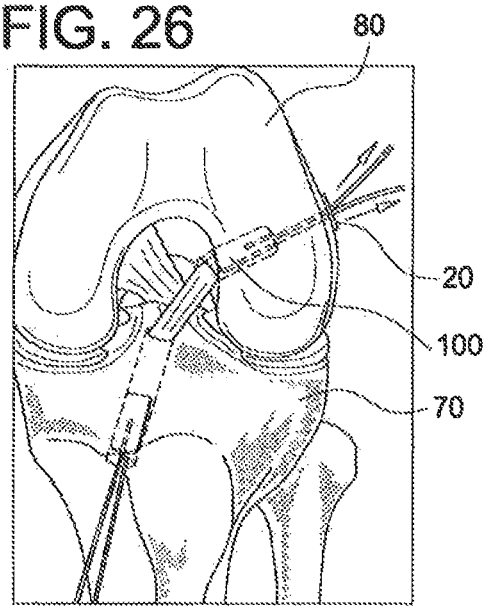
Figure 27:
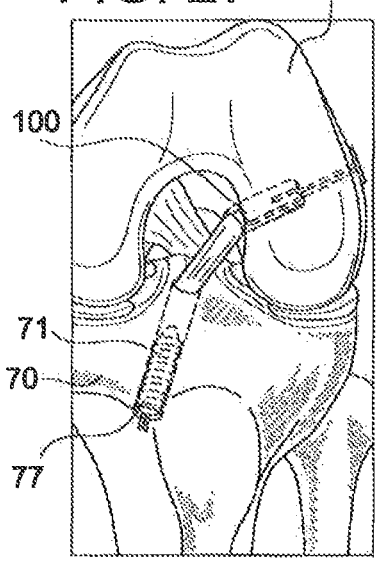

FIG. 26: Hold slight tension on the tibial graft sutures during graft advancement. To advance the graft 90, pull on the tensioning strands one at a time, alternating approximately 2 cm on each side. Once the graft is fully seated, pull firmly back on the graft to check fixation. Once the graft is seated, do not continue to pull tensioning strands.

Figure 28:
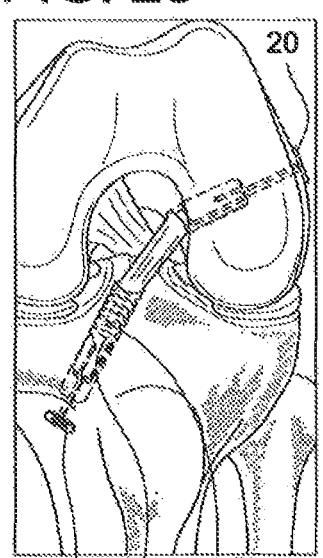
Figure 29:
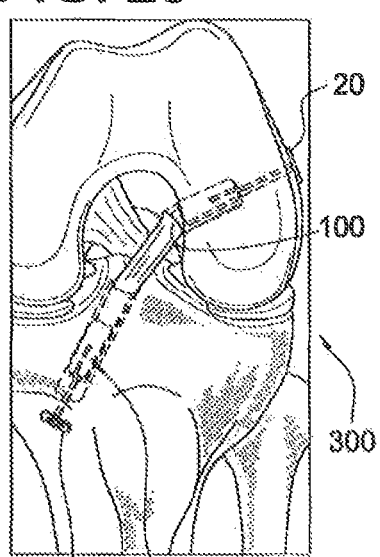

FIGS. 27-30: Fix the tibial side of the graft (in tibial tunnel 71 of tibia 70) and cut shortening strands. BTB TightRope® 99 is also ideal for All-inside® ACL Reconstruction with RetroScrew® (FIG. 28) or for tibial fixation (FIG. 29). For RetroScrew® fixation, the graft is secured in the tibia 70 employing interference screw 77 (FIG. 27) or an interference screw 77 and a button 20a (FIG. 28). Tibial fixation may be also achieved by attaching tensionable construct 99 to the remaining bone block of the BTB graft 90 (in a manner similar to the formation of integrated system 100 for the femoral fixation), to form integrated system 100a for tibial fixation of a final reconstruction construct 300, as shown in FIG. 29.

Figure 30:
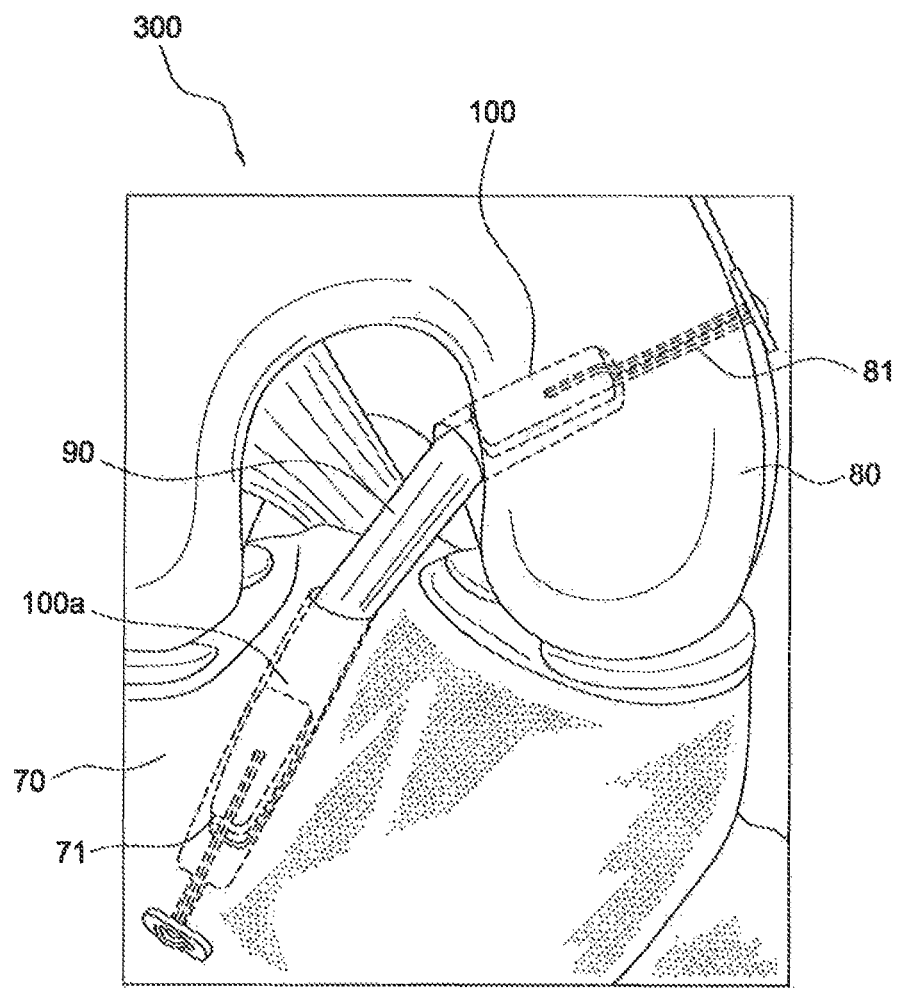

FIG. 30: Shows an enlarged view of the final construct 300 (ACL BTB TightRope®) of FIG. 29, with two integrated systems 100, 100a for the fixation of a BTB graft 90 within femoral socket 81 and tibial socket 71.

FIGS. 31-40 show an example of an Open Tightrope ABS 199 which is passed through a soft tissue graft 390 that has been stitched together (with stiches 322), not allowing loading over a traditional "closed loop" device. This exemplary embodiment employs a tensionable construct 199 which is similar to the tensionable construct 99 described above in that it also contains an adjustable knotless loop 50 and a splicing device 40 (a suture passing instrument or any shuttle/pull device to form a final splice in the construct); however, tensionable construct 199 differs from the tensionable construct 99 in that it does not include a fixation device 20 (button 20). As in the previously-described embodiments, loop 50 is passed through soft tissue graft 390 and then the free strand 5b of the construct 199 is passed through looped portion 50c of the knotless, adjustable loop 50 and through the pre-loaded passing suture loop 40 (splicing device 40). A second splice is formed in the flexible strand 5 and a second loop 55 is interconnected to loop 50 (through interconnecting region 59) forming close loop 150 having an adjustable, knotless configuration. Upon fixation of the graft 390 in a bone tunnel (for example, the tibial tunnel), a slotted button (having a dog bone configuration, for example) may be employed to secure the construct to the tibial cortex.

Figure 31:
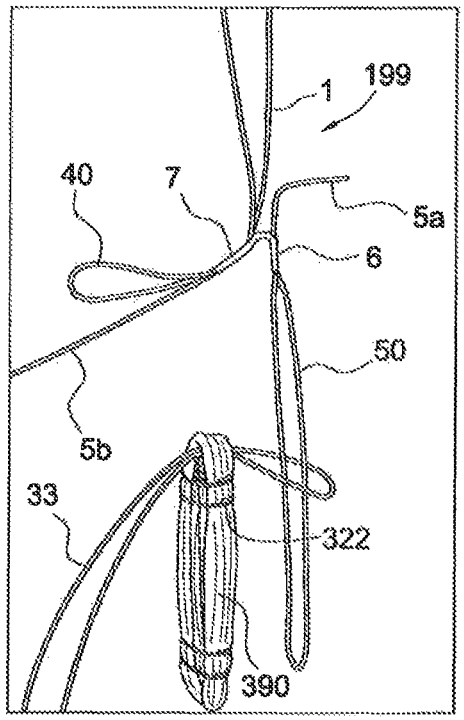
Figure 32:
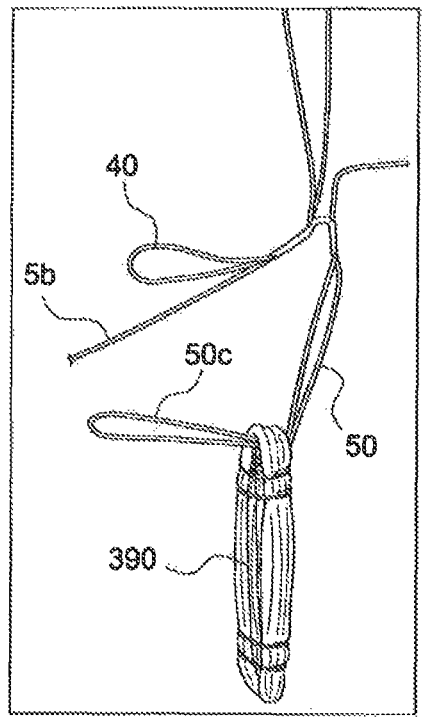

FIGS. 31 and 32: The looped side 50 of the tensionable construct 199 is passed through the graft 390 with a passing suture 33 (FIG. 31) to form loop portion 50c extending out of the tissue graft (FIG. 32).

Figure 33:
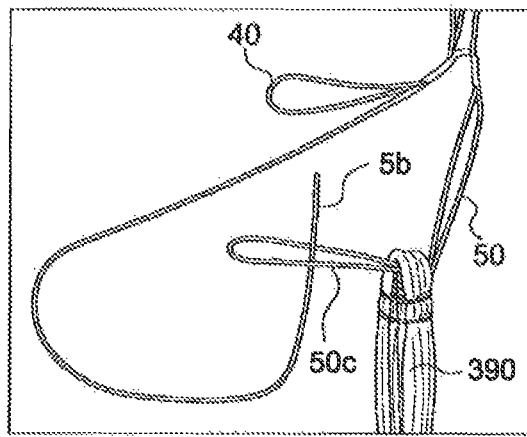
Figure 34:
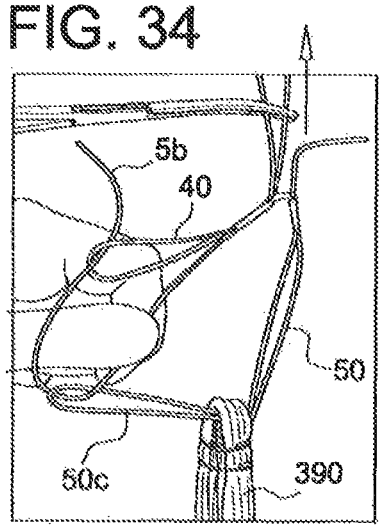

FIGS. 33-35: The free end 5b is passed through the loop 50c (FIG. 33), and then placed in the passing suture 40 (FIG. 34) where it is pulled through the splice 7 to create the tightrope "closed loop" 150 (FIG. 35) of integrated assembly 200a including tensionable construct 199a (without the splicing suture 40). In this manner, by pulling the passing suture 40, end 5b passes through splice 7 and forms another closed loop 55 which is interconnected with loop 50 by interconnecting region 59. The overall construct is an adjustable, knotless, closed loop 150 formed of two interconnected loops 50, 55 and two splices 6, 7 (all formed from a single, same suture strand 5).

FIG. 36: TightRope® loop is assembled and ready to be passed into socket, for example tibial socket 71 in tibia 70. The TightRope® 199a and graft 290 are passed into the tibia 70.

FIGS. 37-40: A slotted button 120 (FIGS. 37-39) is loaded onto the tightrope loop and tensioned against bone which tensions and fixates the graft. The final construct 400 is shown in FIG. 40 with integrated system 200a implanted into tibia and secured to the tibial cortex with button 120.

The tensionable constructs of the present invention (which are employed for further attachment to a graft and for subsequent implantation into a surgical site) may be provided in a pre-assembled state, on an assembly board which may be part of a surgical kit. The assembly board may contain the tensionable construct with the flexible closed loop (adjustable, self-locking knotless flexible closed loop), the splicing device (shuttle/pull device), any passing suture for the fixation device (if a fixation device is employed), and a needle, all pre-assembled and ready for use by medical personnel. Instructions may be also provided.

FIG. 41 illustrates an exemplary sterilizable assembly board 500 with an exemplary adjustable tensionable construct 99 of the invention (pre-assembled tensionable construct 99), a needle, and any other necessary components. The assembly board may be folded, and will be supplied with mounted components, as a sterilized product, e.g., a kit.

In use, while the suture construct of the invention is maintained in position by a plurality of flexible holding tabs 510, the needle 4 with the threaded loop 50 are lifted from the board and passed through an opening in the BTB graft block. After the threaded loop 50 emerges from the bone block opening, the needle 4 is cut off. A free end 5b of the suture is then removed from the board tabs and is passed through the emerged threaded loop section 50c. Then the blue splicing loop 40 is lifted from the board tabs and the free end 5b is passed through the lifted loop 40. The free suture strand is then pinched against an adjacent section of the free suture strand to form a temporary loop that captures splicing loop section 50c. The knotted end 11 of the splicing loop 40 is pulled until the temporary loop is in vicinity of the button 20. Then the free suture strand end is pulled through the button hole. The BTB graft 90 is held while the free end is pulled to even out the loops holding the BTB graft 90. The assembled BTB graft construct and passing suture are then removed from the assembly board.

Figure 42:
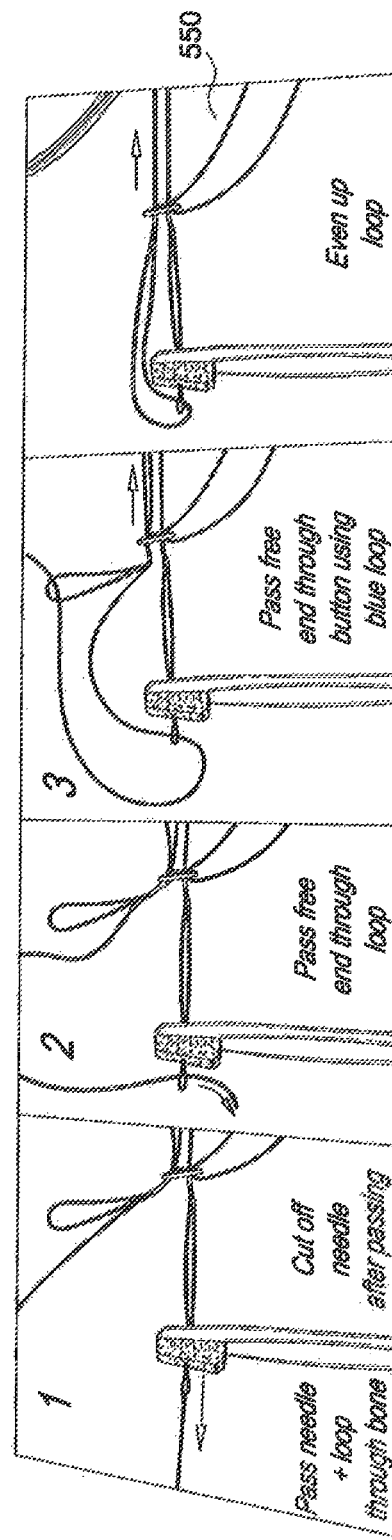
FIG. 42 illustrates an exemplary "direction of use" card to assist surgeon(s) in attaching the mounted self-locking, adjustable button/loop construct of FIG. 41 with a graft (soft tissue graft or BTB graft).

FIG. 42 shows an exemplary instruction card 550 that may be part of the kit of the present invention together with the assembly board 500.

The tensionable, self-locking adjustable constructs of the present invention are provided around a BTB bone block without forming any knots or any crossing of the loop strands between the top of the bone block and the button. This minimizes the compressive forces on the bone block which, in turn, leads to a stronger reconstruction. The absence of any knots also limits the chances of the knot tightening down and restricting the adjustability of the implant.

The present invention also provides methods of tissue repair/reconstruction by inter alia: (i) providing a surgical reconstruction system comprising an adjustable, self-locking, knotless loop construct including an adjustable loop formed of two interconnected loops and two splices and, optionally, a button attached to the adjustable loop; and (ii) securing tissue (for example, soft tissue or BTB graft) with the reconstruction system.

An exemplary method of BTB ACL reconstruction comprises inter alia the steps of: (i) providing a flexible, adjustable, knotless button/loop construct 99 with a fixation device (button) 20 attached to the button/loop construct that is capable of adjusting tension, the button/loop construct 99 including an adjustable loop 50 and a non-adjustable, fixed loop 40 and two corresponding eyesplices 6, 7; (ii) passing the adjustable loop 50 through a hole 91a formed in a bone block 91 of a BTB graft 90; (iii) passing the free strand 5b through the looped end 50 of the construct; (iv) passing the free strand 5b through the fixed loop 40 (of the pre-loaded passing suture 1); (v) pulling the tails of the pre-loaded passing suture 1 through the construct to shorten the construct, as desired; and (vi) securing the BTB graft 90 within a femoral tunnel/socket by pulling on button 20. The construct is adjustable in length and allows the surgeon the ability to customize the device to each patient and seat the bone block fully against the back wall of the femoral socket. The adjustments are self-locking and the fixation device (implant) minimizes the compressive forces on the bone block.

Button 20 of the reconstruction integrated assembly 100 may be formed, for example, of metal, PEEK or PLLA. As detailed above, the button is provided with openings that allow the passage of the flexible materials to pass thereto. The flexible materials may be a high strength braid construct such as an ultrahigh molecular weight (UHMWPE) braid. As detailed above, the flexible materials may be provided with optional colored strands (for example, white and blue) to assist surgeons in distinguishing between suture lengths with the trace and suture lengths without the trace.

The flexible strands employed for the constructs of the present invention may be formed of a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The strands may also be formed of a stiff material, or combination of stiff and flexible materials, depending on the intended application. The strands may be also coated and/or provided in different colors. The knotless constructs of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

The invention claimed is:

1. A method of tissue repair/reconstruction, comprising:
attaching a tensionable construct to a bone-tendon-bone (BTB) graft to establish an integrated construct, wherein the tensionable construct includes a fixation device and an adjustable, self-locking, knotless, flexible loop connected to the fixation device,
wherein a region where two flexible loop portions of the adjustable, self-locking, knotless, flexible loop interlink is located within a hole of a bone block of the BTB graft;
passing the fixation device through a bone tunnel to position the adjustable, self-locking, knotless, flexible loop within the bone tunnel; and
adjusting a length of the adjustable, self-locking, knotless, flexible loop to secure the BTB graft at least partially within the bone tunnel.

2. The method as recited in claim 1, wherein the fixation device is a button.

3. The method as recited in claim 1, wherein adjusting a length of the adjustable, self-locking, knotless, flexible loop includes:
tensioning a shortening strand of the adjustable, self-locking, knotless, flexible loop.

4. The method as recited in claim 1, comprising:
attaching a second tensionable construct to the BTB graft, wherein the second tensionable construct includes a second fixation device and a second adjustable, self-locking, knotless, flexible loop connected to the second fixation device.

5. The method as recited in claim 4, wherein the adjustable, self-locking, knotless, flexible loop is attached to a first bone block of the BTB graft, and the second adjustable, self-locking, knotless, flexible loop is attached to a second bone block of the BTB graft, wherein a tendon extends between the first bone block and the second bone block.

6. The method as recited in claim 4, comprising:
positioning the second adjustable, self-locking, knotless, flexible loop within a second bone tunnel; and
adjusting a length of the second adjustable, self-locking, knotless, flexible loop to secure the BTB graft within the second bone tunnel.

7. A method of tissue repair/reconstruction, comprising:
attaching a tensionable construct to a bone-tendon-bone (BTB) graft to establish an integrated construct, wherein the tensionable construct includes a fixation device and an adjustable, self-locking, knotless, flexible loop connected to the fixation device;
passing the fixation device through a bone tunnel to position the adjustable, self-locking, knotless, flexible loop within the bone tunnel; and
adjusting a length of the adjustable, self-locking, knotless, flexible loop to secure the BTB graft at least partially within the bone tunnel,
wherein attaching the tensionable construct to the BTB graft includes:
passing a first looped limb of the adjustable, self-locking, knotless, flexible loop through a hole formed in a bone block of the BTB graft with a needle;
passing a straight limb of the adjustable, self-locking, knotless, flexible loop through the first looped limb; and
connecting the straight limb to a splicing device of the tensionable construct.

8. The method as recited in claim 7, comprising:
pulling the splicing device to deliver the straight limb through a splice of the adjustable, self-locking, knotless, flexible loop.

9. The method as recited in claim 8, wherein, once delivered through the splice, the straight limb establishes a shortening strand of the adjustable, self-locking, knotless, flexible loop.

10. The method as recited in claim 7, wherein the splicing device is a fixed loop, a nitinol loop, or a second needle.

11. A method of tissue repair/reconstruction, comprising:
passing a first portion of an adjustable, self-locking, knotless, flexible loop of a tensionable construct through a hole formed in a first bone block of a bone-tendon-bone (BTB) graft, wherein the tensionable construct includes a fixation device attached to the adjustable, self-locking, knotless, flexible loop;
passing a second portion of the adjustable, self-locking, knotless, flexible loop through the first portion of the adjustable, self-locking, knotless, flexible loop that is passed through the hole of the first bone block;
splicing the second portion of the adjustable, self-locking, knotless, flexible loop through a third portion of the adjustable, self-locking, knotless, flexible loop to secure the adjustable, self-locking, knotless, flexible loop to the BTB graft;
passing the fixation device through a bone tunnel to position the adjustable, self-locking, knotless, flexible loop within the bone tunnel; and adjusting a length of the adjustable, self-locking, knotless, flexible loop to secure the first bone block within the bone tunnel.

12. The method as recited in claim 11, wherein passing the first portion of the adjustable, self-locking, knotless, flexible loop includes:
 pulling the first portion through the hole of the first bone block with a needle.

13. The method as recited in claim 11, wherein the first portion of the adjustable, self-locking, knotless, flexible loop is a looped limb of the adjustable, self-locking, knotless, flexible loop.

14. The method as recited in claim 11, wherein passing the second portion of the adjustable, self-locking, knotless, flexible loop includes:
 subsequent to passing the first portion through the hole, passing the second portion through an opening established by the first portion of the adjustable, self-locking, knotless, flexible loop.

15. The method as recited in claim 11, wherein the second portion of the adjustable, self-locking, knotless, flexible loop is a straight limb of the adjustable, self-locking, knotless, flexible loop.

\* \* \* \* \*